United States Patent
Matsuda et al.

(10) Patent No.: US 7,810,249 B2
(45) Date of Patent: Oct. 12, 2010

(54) PROGRAM TO MAKE OF CUTTING DATA FOR INNER FACE OF DENTAL PROSTHESIS

(75) Inventors: Yoshinori Matsuda, Itabashi-ku (JP); Tatsuru Doumoto, Itabashi-ku (JP); Yoshinori Ebihara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 641 days.

(21) Appl. No.: 11/840,782

(22) Filed: Aug. 17, 2007

(65) Prior Publication Data

US 2008/0177409 A1    Jul. 24, 2008

(30) Foreign Application Priority Data

Aug. 17, 2006    (JP) ............... 2006-222651

(51) Int. Cl.
    *A61C 19/04*    (2006.01)
    *G06F 19/00*    (2006.01)
(52) U.S. Cl. .................. 33/513; 702/155; 700/118
(58) Field of Classification Search ................. 33/503, 33/513; 700/117, 118; 702/155
    See application file for complete search history.

(56) References Cited

U.S. PATENT DOCUMENTS

| 5,092,022 | A | * | 3/1992 | Duret ..................... 700/163 |
| 5,587,912 | A | * | 12/1996 | Andersson et al. ........... 700/98 |
| 6,766,217 | B1 | * | 7/2004 | Hamada ................... 700/163 |
| 7,013,191 | B2 | | 3/2006 | Rubbert et al. |
| 2002/0081554 | A1 | * | 6/2002 | Marshall et al. ............... 700/98 |
| 2002/0102520 | A1 | | 8/2002 | Liyama et al. |
| 2004/0158342 | A1 | * | 8/2004 | Wolf et al. ................... 700/98 |
| 2006/0004477 | A1 | * | 1/2006 | Kopelman et al. .......... 700/118 |
| 2006/0253215 | A1 | * | 11/2006 | Weber et al. ................. 700/98 |
| 2009/0325127 | A1 | * | 12/2009 | Kusch et al. ................. 700/98 |
| 2010/0086899 | A1 | * | 4/2010 | Holzner et al. ............. 700/118 |
| 2010/0105008 | A1 | * | 4/2010 | Powell et al. ................. 700/98 |
| 2010/0124731 | A1 | * | 5/2010 | Groscurth et al. .......... 700/119 |

FOREIGN PATENT DOCUMENTS

| EP | 1 088 620 A1 | 4/2001 |
| EP | 1 293 174 A1 | 3/2003 |
| JP | 57-200144 | 12/1982 |
| JP | 2002-224142 | 8/2002 |
| JP | 2002-336277 | 11/2002 |
| JP | 2003-61981 | 3/2003 |
| WO | WO 01/91664 A1 | 12/2001 |

* cited by examiner

*Primary Examiner*—G. Bradley Bennett
(74) *Attorney, Agent, or Firm*—Oblon, Spivak, McClelland, Maier & Neustadt, L.L.P.

(57) ABSTRACT

To remove an undercut part from three-dimensional data of the inner face, the program includes a surface model creating means to create a surface model based on three-dimensional data of a gypsum model including an abutment tooth, a cutting direction specifying means to specify a direction of a cutting bar, and a surface model creating means to create a surface model for machining by changing the three-dimensional data to have new coordinates by determining a base axis in parallel with the cutting bar in the surface model and plane moving coordinates of the cutting bar, and converting the coordinates of a point which becomes an undercut part, to be equal to the plane moving coordinates of a point having a high height from a specified face rectangular to the base axis at the opposite side of the occlusion face and a long distance from the base axis.

6 Claims, 2 Drawing Sheets

PROGRAM TO MAKE OF CUTTING DATA FOR INNER FACE OF DENTAL PROSTHESIS

BACKGROUND OF THE INVENTION

1. Field of the Invention

The present invention relates to a program to make of cutting data for inner face of a dental prosthesis at a time of producing a dental prosthesis by cutting a block material using a CAD/CAM system.

2. Description of the Conventional Art

A dental prosthesis is produced by cutting a block material using a CAD/CAM system through the steps of taking an impression of the inside of an oral cavity (a teeth shape or a dentition shape) of a patient using a dental impression material, where the impression includes an abutment tooth of a portion for which the dental prosthesis is produced, producing a gypsum model based on the impression, and measuring three-dimensional coordinates information of dentition shapes using a laser measuring device, where the dentition shapes are a dentition shape on the side of a portion for which a dental prosthesis of the gypsum model is produced and a dentition shape on an opposite tooth side of the portion.

Then, a dental prosthesis, that is, a coping (an inner crown), a crown, or a bridge is designed based on the measured data. At this time, a designing operation to match a margin of a dental prosthesis with a margin line of an abutment tooth at which the dental prosthesis is fixed, a designing operation to keep a cement space at an inner face of a dental prosthesis, and a designing operation for the outer face of a dental prosthesis are carried out (for example, refer to Japanese Patent Application Laid Open No. 2002-224142, and FIG. 13 of Domestic Re-publication of PCT International Publication No. WO01/091664). When designing of a dental prosthesis is thus finished, a block material to be machined is selected, and an objective dental prosthesis is cut using an automatic cutting machine, and is subjected to trimming. Then, production of a dental prosthesis is completed. In such a dental CAD/CAM system, as a device to input three-dimensional coordinates information of a gypsum model including teeth to be treated, e.g., teeth needing a dental prosthesis, or the like, for example, a device to obtain three-dimensional shape data in a non-contact state by directly irradiating light to a gypsum model using an optical fiber and receiving the reflected light (for example, refer to Japanese Patent Application Laid Open No. 2002-224142), and a device to obtain three-dimensional shape data in a non-contact state by directly irradiating laser to a gypsum model (for example, refer to FIG. 13 of Domestic Re-publication of PCT International Publication No. WO01/091664) are used. Further, a device to obtain three-dimensional shape data by measuring the surface of a gypsum model by using a probe as a contact is also used (for example, refer to Japanese Patent Applications Laid Open No. 57-200144, 2002-336277, and 2003-61981).

Among the above-described measuring devices, an excellent three-dimensional measuring device which can lower a production cost and a maintenance cost because of having only one laser sensor to measure a shape of a gypsum model to be measured, is a three-dimensional measuring device having a rotary table in which an axis of a rotary shaft is along z axis, a mounting table fixedly provided on the rotary table to set a measured object mounting tool, and a measuring part to measure the three-dimensional coordinates (x, y, z) of the shape of a gypsum model to be measured, which is mounted on the measured object mounting tool on the mounting table, by one laser sensor capable of rotating and moving on the same plane including z axis around a desired point on the z axis at least. In such a dental CAD/CAM system, movement of a cutting bar of a general automatic cutting machine is limited to those on one plane with respect to a block for cutting and in the axial direction of the cutting bar, as illustrated in FIGS. 5 and 6 of Japanese Patent Application Laid Open No. 2003-61981. Thus, when the data for cutting an inner face of a dental prosthesis includes an under cut portion in the axial direction of a cutting bar, a portion which cannot be cut becomes to exist. Here, an under cut portion is a more recessed portion than a already cut portion when a cutting bar cut a certain portion and further advances to cut in a axial direction of the cutting bar. Further, in a dental CAD/CAM system, a program is generally made to stop cutting work when a portion which cannot be cut exists. Therefore, there is a problem that cutting may be not finished.

The reason of generating such a phenomenon is as follows. When data for cutting the inner face of a dental prosthesis is produced, the three-dimensional coordinates of a portion for which a dental prosthesis is produced are faithfully measured from a gypsum model and the coordinates are used as they are. Thus, when the longitudinal section of the three-dimensional coordinates-measured gypsum model includes a recessed part in a portion at the tooth root side than the occlusion face side of an abutment tooth, data for cutting the inner face of a dental prosthesis is produced while missing the existence of the recessed part. That is, when the data for cutting the inner face of a dental prosthesis is produced, the inner face except a portion of a margin line is automatically designed so as to keep a cement space having an approximately fixed thickness from the outer face of an abutment tooth. Thus, when the longitudinal section of the three-dimensional coordinates-measured gypsum model includes a recessed part in a portion at the tooth root side than the occlusion face side of an abutment tooth, the inner face is designed to have a projected part according to the shape of the recessed part.

Therefore, it is necessary to make data for cutting the inner face of a dental prosthesis while taking care so as not to form an under cut part in the axial direction of a cutting bar. However, it is hard in fact to carry out the operation to remove an under cut part while confirming three-dimensional data on a monitor, and much time is needed. Further, an under cut part is hardly displayed on a screen depending on a shape. Thus, data for cutting the inner face of a dental prosthesis is finally produced having an under cut part in the axial direction of a cutting bar, so that the actual cutting may be interrupted.

SUMMARY OF THE INVENTION

In order not to include an under cut part in the axial direction of a cutting bar in three-dimensional data of the inner face of a dental prosthesis to be cut in a CAD/CAM system, an objective of the present invention is to provide a program to support production of data for cutting the inner face of dental prosthesis, so that the program makes it possible to remove a portion of an under cut part in the axial direction of a cutting bar on the inner face of a dental prosthesis from the three-dimensional coordinates measured from a gypsum model which reproduces the shape of an abutment tooth as a base to produce data for cutting the inner face of dental prosthesis.

The earnest work was carried out in order to solve the above-described problems and, as a result of this, present inventors found out the followings to compete the present invention. In three-dimensional coordinates data measured from a gypsum model which reproduces the shape of an abutment tooth and is a base to produce data for cutting an inner face of a dental prosthesis, a portion to form an under cut part in the axial direction of a cutting bar to cut the inner face of a dental prosthesis to be cut cannot be seen when the gypsum model reproducing the shape of an abutment tooth is seen from the occlusion face side in parallel with the axial direction of the cutting bar. Then, new three-dimensional data is created by re-calculating the plane coordinates of a not-appearing portion, which does not appear on a plane view when a gypsum model reproducing the shape of an abutment tooth is seen from the occlusion face side in parallel with the axial direction of a cutting bar, to plane coordinates of an appearing portion, which continues from the not-appearing portion and appears on the plane view. Accordingly, when three-dimensional data of the inner face of a dental prosthesis is produced based on the created new three-dimensional data, there is no under cut part in the axial direction of a cutting bar.

That is, the present invention is a program to make of cutting data for inner face of a dental prosthesis, and the program includes, a surface model creating means to create a surface model of a portion at which a dental prosthesis is mounted, based on three-dimensional data obtained by a three-dimensional measuring device to measure the three-dimensional coordinates (x, y, z) of the shape of a gypsum model including an abutment tooth, a cutting direction specifying means to specify a direction of a center shaft of a cutting bar of an automatic cutting machine to cut a dental prosthesis to be produced, where the direction is specified with respect to the surface model, and a surface model for machining creating means to create a surface model for machining by the steps of adjusting a basic axis (z axis) of the three-dimensional data of the surface model created by the surface model creating means so as to be in parallel with the center shaft of the cutting bar, changing the three-dimensional data of the surface model to three-dimensional data having new coordinates by determining plane moving coordinates (X axis and Y axis) of the cutting bar of an automatic cutting machine for cutting a dental prosthesis in a view in which the surface model is seen from the occlusion face side in parallel with the center shaft of the cutting bar, and determining a base axis (Z axis) in the surface model, and converting the plane moving coordinate of a point which is on the straight line being rectangular to the base axis and crossing the base axis on the cross sectional plane of the changed new three-dimensional data, to be equal to the plane moving coordinates of a point having the highest height from a specified face being rectangular to the base axis at the opposite side of the occlusion face of the surface model, where the distance from the base axis to the point on the straight line is shorter than the distance from the base axis to a point having a high height from the specified face.

Further, the present inventors found out the followings. In such a program to support production of data for cutting the inner face of a dental prosthesis, the surface model for machining creating means uses the intersection point of the maximum lengths (X max, Y max) on the plane moving coordinates of an outline of a surface model as a base axis (Z axis) on the plane view of three-dimensional data. Accordingly, the base axis for cutting a block material to form the inner face of a dental prosthesis is accurately set in the surface model for machining. Further, since the distance from the base axis to the cutting face is not largely varied, an operator of an automatic cutting machine can easily image invasion of a cutting bar to the block material while having a good sense. So, it is preferable.

The program further includes a pre-conversion surface model displaying means to display a plan view of three-dimensional data, in which the plane moving coordinates are not converted yet to be equal to the plane moving coordinates of a point having the highest height, on a monitor. Accordingly, an operator of an automatic cutting machine can operate to set the base axis with selecting an angle to incline the pre-conversion surface model so as to reduce the under cut part to a minimum, while imaging the base axis of a cutting bar invading to the block material and confirming a screen. Thus, an operator of an automatic cutting machine can have a good sense, so that it is preferable.

The surface model for machining creating means can particularly designate a portion of a point, at which the plane moving coordinates are changed by the surface model for machining creating means, from a surface model displayed on a monitor by the pre-conversion surface model displaying means. Accordingly, since the plane moving coordinates are not changed with respect to the whole surface model but changed in only a portion being necessary to be changed, the number of calculation can decrease. Therefore, the operating efficiency can be improved, so that it is preferable.

During the time of changing three-dimensional data of a surface model to three-dimensional data having new coordinates, the surface model for machining creating means can convert the plane moving coordinates of a point, which is on the straight line crossing the base axis on the cross sectional plane of three-dimensional data to be changed, to be equal to the plane moving coordinates of a point having the highest height from a specified face being rectangular to the base axis at the opposite side of the occlusion face of the surface model in order to create a surface model for machining, where the distance from the base axis to the point on the straight line is shorter than the distance from the base axis to a point having a high height from the specified face. Accordingly, two operations that a whole three-dimensional data of a surface model is changed to three-dimensional data having new coordinates, and thereafter, the changed three-dimensional data is further changed to new three-dimensional data of a surface model for machining not having an under cut part are not necessary. Thus, the operating efficiency is improved, so that it is preferable.

The program further includes a basic surface model displaying means to display the shape of a surface model created by the surface model creating means on a monitor, and the basic surface model displaying means includes an angle specifying means to specify the basic axis (z axis) of the three-dimensional data of the surface model, which is created by the surface model creating means, to be in parallel with the center shaft of a cutting bar. Accordingly, an operator of an automatic cutting machine can easily set an angle of the base axis (Z axis) with respect to the basic axis (z axis) to a proper angle while imaging the base axis (Z axis) of a cutting bar invading to a block material. So, it is preferable.

The present invention is a program to support production of data for cutting the inner face of a dental prosthesis in which an under cut part is completely removed from three-dimensional data of an object to be measured. Thus, when a block material is cut to produce a dental prosthesis using a CAD/CAM system, the present invention can surely prevent occurring of a phenomenon to interrupt a processing operation due to an existence of an under cut part.

BRIEF EXPLANATION OF DRAWINGS

FIG. 6 is an explanatory plan view of FIG. 5.

FIG. 7 is an explanatory view to illustrate a surface model for machining created by a surface model for machining creating means.

DETAILED DESCRIPTION OF PREFERRED EMBODIMENT

The present invention is a program to support production of data for cutting the inner face of a dental prosthesis, and the program includes, a surface model creating means to create a surface model of a portion at which a dental prosthesis is mounted, where the portion is produced based on three-dimensional data obtained by a three-dimensional measuring device configured to measure the three-dimensional coordinates (x, y, z) of the shape of a gypsum model including an abutment tooth, a cutting direction specifying means to specify a direction of a center shaft of a cutting bar of an automatic cutting machine to cut a dental prosthesis to be produced, where the direction is specified with respect to the surface model, and a surface model for machining creating means to create a surface model for machining by the steps of adjusting a basic axis (z axis) of the three-dimensional data of the surface model created by the surface model creating means so as to be in parallel with the center shaft of the cutting bar, changing the three-dimensional data of the surface model to three-dimensional data having new coordinates by determining plane moving coordinates (X axis and Y axis) of the cutting bar of an automatic cutting machine for cutting a dental prosthesis in a view in which the surface model is seen from the occlusion face side in parallel with the center shaft of the cutting bar and determining a base axis (Z axis) in the surface model, and converting the plane moving coordinate of a point which is on the straight line being rectangular to the base axis and crossing the base axis on the cross sectional plane of the changed new three-dimensional data, to be equal to the plane moving coordinates of a point having the highest height from a specified face being rectangular to the base axis on the opposite side of the occlusion face of the surface model, where the distance from the base axis to the point on the straight line is shorter than the distance from the base axis to a point having a high height from the specified face.

The program to support production of data for cutting the inner face of a dental prosthesis according to the present invention will be described in detail below with reference to drawings.

Figure 1:
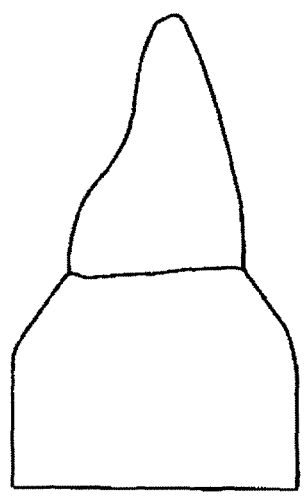
FIG. 1 is a front view of a portion for which a dental prosthesis is produced according to a gypsum model produced based on an impression taken from the inside of an oral cavity of a patient, where the portion includes an abutment tooth.
Figure 2:
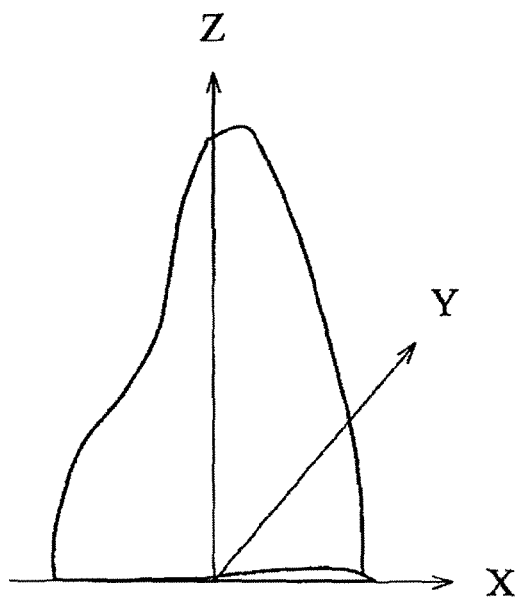
FIG. 2 is an explanatory front view to illustrate three-dimensional coordinates (x, y, z) measured from the gypsum model in FIG. 1.
Figure 3:
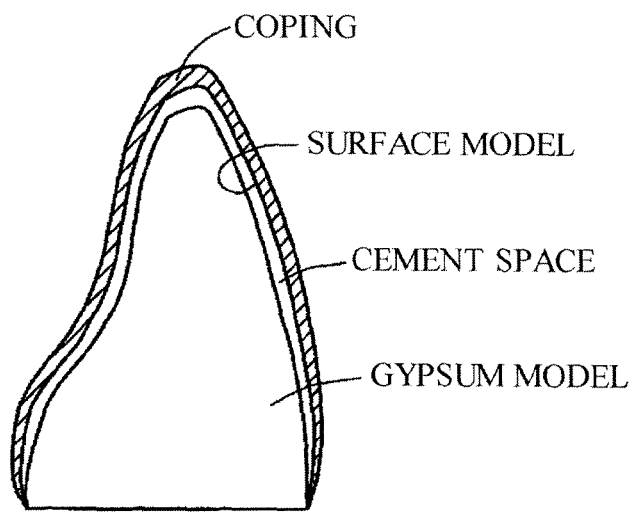
FIG. 3 is an explanatory view to illustrate a surface model of a portion at which a dental prosthesis to be produced by a surface model creating means based on three-dimensional data measured in FIG. 2 is mounted, and illustrate a coping as a dental prosthesis to be produced.
Figure 4:
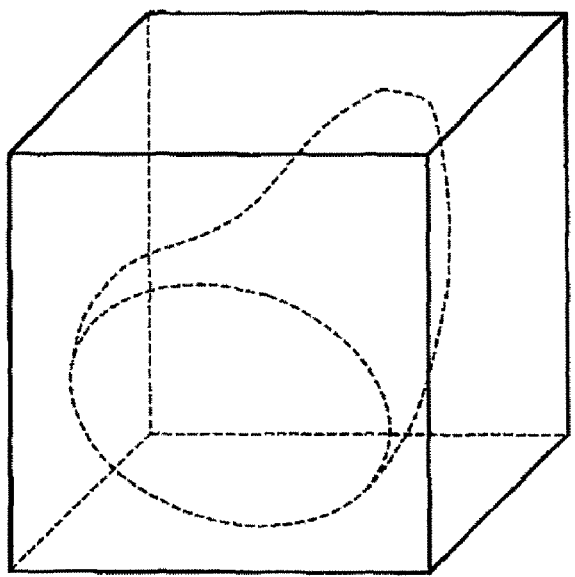
FIG. 4 is a perspective explanatory view to schematically illustrate a position of a dental prosthesis to be produced in a block material to be processed.
Figure 5:
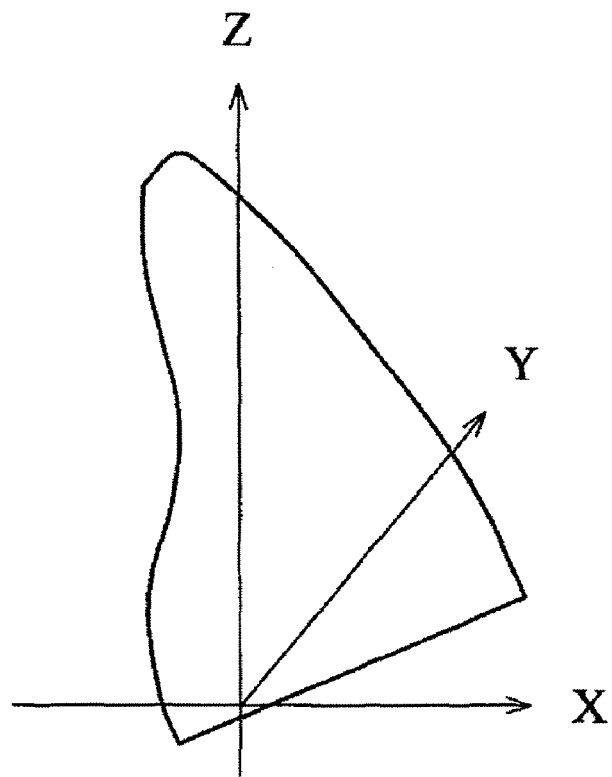
FIG. 5 is an explanatory view to illustrate a state that a cutting direction of a center shaft of a cutting bar of an automatic cutting machine, which is specified by a cutting direction specifying means, is determined with a base axis (Z axis) in a surface model, and three-dimensional data of a surface model is changed to three-dimensional data (X, Y, Z) having new coordinates.

FIG. 1 is a front view of a portion for which a dental prosthesis is produced according to a gypsum model produced based on an impression taken from the inside of an oral cavity of a patient, where the portion includes an abutment tooth. FIG. 2 is an explanatory front view to illustrate three-dimensional coordinates (x, y, z) measured from the gypsum model in FIG. 1. FIG. 3 is an explanatory view to illustrate a surface model of a portion at which a dental prosthesis to be produced by a surface model creating means based on three-dimensional data measured in FIG. 2 is mounted, and illustrate a coping as a dental prosthesis to be produced. FIG. 4 is a perspective explanatory view to schematically illustrate the position of a dental prosthesis to be produced in a block material to be processed. FIG. 5 is an explanatory view to illustrate a state that the cutting direction of a center shaft of a cutting bar of an automatic cutting machine, which is specified by a cutting direction specifying means, is determined with a base axis (Z axis) in a surface model, and three-dimensional data of a surface model is changed to three-dimensional data (X, Y, Z) having new coordinates. FIG. 6 is an explanatory plan view of FIG. 5. FIG. 7 is an explanatory view to illustrate a surface model for machining created by a surface model for machining creating means.

The program to make of cutting data for inner face of a dental prosthesis according to the present invention includes the steps of taking an impression of a portion for which a dental prosthesis is produced including an abutment tooth in the inside of an oral cavity (a teeth shape and a dentition shape) of a patient using a dental impression material, producing a gypsum model based on the impression as illustrated in FIG. 1, and measuring three-dimensional coordinates information of a portion at which a dental prosthesis according to the gypsum model is produced, using a laser measuring device or the like as illustrated in FIG. 2. In order to measure the three-dimensional coordinates information, it is preferable to use a three-dimensional measuring device including a rotary table in which an axis of a rotary shaft is z axis, a mounting table which is fixedly provided on the rotary table and can be provided with a measured object mounting tool, and a measuring part to measure the three-dimensional coordinates (x, y, z) of a shape of a gypsum model to be measured by one laser sensor capable of rotating and moving on a same plane including the z axis around a desired point on at least the z axis, where the gypsum model is mounted to the measured object mounting tool on the mounting table.

Accordingly, the surface model creating means creates a surface model of a portion at which a dental prosthesis to be produced is mounted as illustrated in FIG. 3 based on three-dimensional data measured by the three-dimensional measuring device to measure the three-dimensional coordinates (x, y, z) of a shape of the gypsum model including an abutment tooth. The surface model is created by a designing operation to match a margin of a dental prosthesis with a margin line of an abutment tooth at which a dental prosthesis is fixed and a designing operation to keep a cement space on the inner face of a dental prosthesis.

Next, the cutting direction specifying means specifies the direction of a center shaft of a cutting bar of an automatic cutting machine to cut a dental prosthesis to be produced, where the direction is specified with respect to the surface model created by the surface model creating means. The cutting direction specifying means specifies the direction of a center shaft of a cutting bar of an automatic cutting machine with respect to a block material to cut a dental prosthesis. By this specification, an efficient arrangement of a cutting bar in a block material to cut a dental prosthesis to be produced so as to obtain the dental prosthesis from a small block material, reduction of the generating amount of cutting chips of a block material, or an effective movement of a cutting bar of an automatic cutting machine so as to obtain a dental prosthesis in a short time can be realized.

Then, the surface model for machining creating means creates a surface model for machining not having an under cut part shown with a broken line as illustrated in FIG. 7 by the steps of adjusting a basic axis (z axis) of the three-dimensional data of the surface model created by the surface model creating means so as to be in parallel with the center shaft of the cutting bar, changing the three-dimensional data of the surface model to three-dimensional data having new coordinates by determining plane moving coordinates (X axis and Y axis) of the cutting bar of an automatic cutting machine for cutting a dental prosthesis in a view in which the surface model is seen from the occlusion face side in parallel with the center shaft of the cutting bar and determining a base axis (Z axis) in the surface model, and converting the plane moving coordinate of a point which is on the straight line being rectangular to the base axis and crossing the base axis on the cross sectional plane of the changed new three-dimensional data, to be equal to the plane moving coordinates of a point having the highest height from a specified face being rectangular to the base axis at the opposite side of the occlusion face of the surface model, where the distance from the base axis to the point on the straight line is shorter than the distance from the base axis to a point having a high height from the specified face.

In the plan view of three-dimensional data as illustrated in FIG. 6, the surface model for machining creating means uses the intersection point of the maximum lengths (X max, Y max) as a base axis (Z axis), where this point is on the plane moving coordinates of an outline of a surface model. Accordingly, the base axis for cutting a block material to form the inner face of a dental prosthesis is accurately set in the surface model for machining. Further, since the distance from the base axis to a cutting face is not largely varied, an operator of an automatic cutting machine can easily image invasion of a cutting bar to the block material while having a good sense. So, it is preferable.

Further, the surface model for machining creating means further includes a pre-conversion surface model displaying means to display a plan view of three-dimensional data, in which the plane moving coordinates are not converted to be equal to the plane moving coordinates of a point having the highest height, on a monitor. Accordingly, an operator of an automatic cutting machine can operate to set the base axis with selecting an angle to incline the pre-conversion surface model so as to reduce the under cut part to a minimum, while imaging the base axis of a cutting bar invading to the block material and confirming a screen. Thus, an operator of an automatic cutting machine can have a good sense, so that it is preferable.

Further, the surface model for machining creating means can particularly designate a portion of a point, at which the plane moving coordinates are changed by the surface model for machining creating means from a surface model displayed on a monitor by the pre-conversion surface model displaying means. Accordingly, since the plane moving coordinates are not changed with respect to the whole surface model but changed in only a portion being necessary to be changed, a number of calculation can decrease. Therefore, an operating efficiency can be improved, so that it is preferable.

Further, during the time of changing three-dimensional data of a surface model to three-dimensional data having new coordinates, the surface model for machining creating means can convert the plane moving coordinates of a point, which is on the straight line crossing the base axis on a cross sectional plane of three-dimensional data to be changed, to be equal to the plane moving coordinates of a point having the highest height from a specified face being rectangular to the base axis at the opposite side of the occlusion face of the surface model in order to create a surface model for machining, where the distance from the base axis to the point on the straight line is shorter than the distance from the base axis to a point having a high height from the specified face. Accordingly, two operations that whole three-dimensional data of a surface model is changed to three-dimensional data having new coordinates and changed three-dimensional data is further changed to new three-dimensional data of a surface model for machining not having an under cut part are not necessary. Thus, the operating efficiency is improved, so that it is preferable.

Furthermore, the program further includes a basic surface model displaying means to display a shape of a surface model created by the surface model creating means on a monitor, and the basic surface model displaying means includes an angle specifying means to specify the basic axis (z axis) of the three-dimensional data of the surface model, which is created by the surface model creating means, to be in parallel with the center shaft of a cutting bar. Accordingly, an operator of an automatic cutting machine can easily set an angle of the base axis (Z axis) with respect to the basic axis (z axis) to a proper angle while imaging the base axis (Z axis) of a cutting bar invading to a block material. So, it is preferable.

As explained above, in a program to support production of data for cutting the inner face of a dental prosthesis according to the present invention, the surface model creating means creates a surface model of a portion, at which a dental prosthesis is mounted, based on three-dimensional data obtained by a three-dimensional measuring device to measure the three-dimensional coordinates (x, y, z) of the shape of a gypsum model including an abutment tooth, the cutting direction specifying means specifies a basic axis (z axis) of the surface model so as to be in the desirable direction in parallel with the direction of a center shaft of a cutting bar of an automatic cutting machine to cut a dental prosthesis to be produced, the surface model for machining creating means creates a surface model for machining by the steps of changing three-dimensional data of a surface model to three-dimensional data having new coordinates by determining a base axis (Z axis) to be in parallel with a center shaft of a cutting bar in the surface model, and converting a portion, which becomes an under cut part when a dental prosthesis is cut by a cutting bar of an automatic cutting machine, to be equal to the plane moving coordinates at the occlusion face side at which the under cut part starts, based on the three-dimensional data having new coordinates. Thus, when the inner face of a dental prosthesis is cut by an automatic cutting machine for cutting a dental prosthesis, three-dimensional data corresponding to the automatic cutting machine can be preferably produced so as not to have an under cut part.

What is claimed is:

1. A non-transitory computer readable medium having a program stored therein that when executed by a processor makes cutting data for inner face of a dental prosthesis, and performs steps comprising:

creating with a surface model creating means a surface model of a portion, at which a dental prosthesis is mounted, based on three-dimensional data obtained by a three-dimensional measuring device to measure the three-dimensional coordinates (x, y, z) of the shape of a gypsum model including an abutment tooth;

specifying with a cutting direction specifying means a direction of a center shaft of a cutting bar of an automatic cutting machine for cutting a dental prosthesis to be produced, the direction being specified with respect to the surface model; and creating with a surface model for machining creating means a surface model for machining by the steps of:

adjusting a basic axis (z axis) of the three-dimensional data of the surface model created by the surface model creating means so as to be in parallel with the center shaft of the cutting bar;

changing the three-dimensional data of the surface model to three-dimensional data having new coordinates by determining plane moving coordinates (X axis and Y axis) of the cutting bar of an automatic cutting machine for cutting a dental prosthesis in a view in which the surface model is seen from the occlusion face side in parallel with the center shaft of the cutting bar, and determining a base axis (Z axis) in the surface model; and converting the plane moving coordinates of a point which is on the straight line being rectangular to the base axis and crossing the base axis on a cross sectional plane of the changed new three-dimensional data, to be equal to the plane moving coordinates of a point having the highest height from a specified face being rectangular to the base axis at the opposite side of the occlusion face of the surface model, the distance from the base axis to the point on the straight line being shorter than the distance from the base axis to the point having a high height from the specified face.

2. The computer program product of claim 1, wherein the surface model for machining creating means uses the intersection point of the maximum lengths (X max, Y max) on the plane moving coordinates of an outline of a surface model as a base axis on the plane view of three-dimensional data.

3. The computer program product of claim 1 or 2, wherein the program further comprises a pre-conversion surface model displaying means to display a plan view of three-dimensional data, in which the plane moving coordinates are not converted yet to be equal to the plane moving coordinates of a point having the highest height, on a monitor.

4. The computer program product of claim 3, wherein the surface model for machining creating means can particularly designate a portion of a point, at which the plane moving coordinates are changed by the surface model for machining creating means, from a surface model displayed on a monitor by the pre-conversion surface model displaying means.

5. The computer program product of claim 1, wherein during the time of changing three-dimensional data of a surface model to three-dimensional data having new coordinates, the surface model for machining creating means can convert the plane moving coordinates of a point, which is on the straight line crossing the base axis on the cross sectional plane of three-dimensional data to be changed, to be equal to the plane moving coordinates of a point having the highest height from a specified face being rectangular to the base axis at the opposite side of an occlusion face of the surface model in order to create a surface model for machining, the distance from the base axis to the point on the straight line being shorter than the distance from the base axis to a point having a high height from the specified face.

6. The computer program product of claim 1, wherein the program further comprises a basic surface model displaying means to display a shape of a surface model created by the surface model creating means on a monitor, and the basic surface model displaying means comprises an angle specifying means to specify the basic axis (z axis) of the three-dimensional data of the surface model, which is created by the surface model creating means, to be in parallel with the center shaft of a cutting bar.

* * * * *